United States Patent
Noda et al.

(10) Patent No.: US 6,530,945 B1
(45) Date of Patent: Mar. 11, 2003

(54) SYSTEM AND METHOD FOR CONTROLLING PATIENT TEMPERATURE

(75) Inventors: Wayne A. Noda, Mission Viejo, CA (US); Peter J. Philips, Trabuco Canyon, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/723,973

(22) Filed: Nov. 28, 2000

(51) Int. Cl.[7] .................................................. A61F 7/00
(52) U.S. Cl. ........................ 607/105; 607/96; 607/113; 62/259.3
(58) Field of Search .................................. 607/105, 104, 607/96, 113, 114; 62/259.3

(56) References Cited

U.S. PATENT DOCUMENTS

| | | |
|---|---|---|
| 4,298,006 A | 11/1981 | Parks |
| 4,819,655 A | 4/1989 | Webler |
| 4,899,741 A | 2/1990 | Bentley et al. |
| 4,941,475 A * | 7/1990 | Williams et al. ............ 128/692 |
| 5,092,841 A | 3/1992 | Spears |
| 5,261,411 A | 11/1993 | Hughes |
| 5,279,598 A | 1/1994 | Sheaff |
| 5,304,214 A | 4/1994 | DeFord et al. |
| 5,346,508 A | 9/1994 | Hastings |
| 5,348,554 A | 9/1994 | Imran et al. |
| 5,385,540 A | 1/1995 | Abbott et al. |
| 5,433,740 A | 7/1995 | Yamaguchi et al. |
| 5,437,673 A | 8/1995 | Baust et al. |
| 5,474,533 A | 12/1995 | Ward et al. |
| 5,549,559 A | 8/1996 | Eshel |
| 5,702,358 A | 12/1997 | Witherspoon et al. |
| 5,733,319 A | 3/1998 | Neilson et al. |
| 5,807,395 A | 9/1998 | Mulier et al. |
| 5,837,003 A * | 11/1998 | Ginsburg ................ 607/106 |
| 5,899,899 A | 5/1999 | Arless et al. |
| 5,975,081 A | 11/1999 | Hood et al. |
| 6,110,168 A | 8/2000 | Ginsburg |
| 6,122,551 A * | 9/2000 | Rudie et al. ............... 607/102 |
| 6,146,411 A | 11/2000 | Noda et al. |
| 6,149,673 A * | 11/2000 | Ginsburg .................. 607/96 |
| 6,149,676 A * | 11/2000 | Ginsburg .................. 607/106 |
| 6,231,594 B1 | 5/2001 | Dae |
| 6,254,626 B1 * | 7/2001 | Dobak, III et al. ......... 607/105 |
| 2001/0041923 A1 * | 11/2001 | Dobak, III ................ 607/108 |

FOREIGN PATENT DOCUMENTS

| | | |
|---|---|---|
| JP | 63-283638 | 11/1988 |
| SU | 0848031 | 10/1979 |
| WO | WO 92/10227 | 6/1992 |

OTHER PUBLICATIONS

U.S. patent application Ser. No. 09/396,200, Balding, pending.
U.S. patent application Ser. No. 09/697,667, Noda et al., pending.
U.S. patent application Ser. No. 09/671,114, Walker et al., pending.
U.S. patent application Ser. No. 09/723,973, Noda et al., pending.
Kawamura et al., Effect of Cooling and Heating on the Regional Distribution of Blood Flow in Fetal Sheep, Journal of Developmental Physiology, 1986, 8, pp. 11–21.
Wright et al., Hypothermia Controlled Reperfusion: Two Non–Pharmacologic Method Which Dimish Ischemia–Reperfusion Injury in Skeletal Muscle, Microcirc. Endoth. Lymphatics, 1989, vol. 5.

* cited by examiner

*Primary Examiner*—Denise L. Esquivel
*Assistant Examiner*—Marc Norman
(74) *Attorney, Agent, or Firm*—John L. Rogitz; Arlyn Alonzo

(57) ABSTRACT

A controller for a heat exchanger that heats and cools saline flowing through a closed loop heat exchange catheter cools the saline to achieve a target temperature, and then immediately upon reaching target temperature heats the saline. Upon detection of, e.g., a slight patient temperature rise, the controller cools the saline again, with the control loop continuing to tightly control patient temperature in a narrow band around the target temperature.

6 Claims, 1 Drawing Sheet

Control Logic

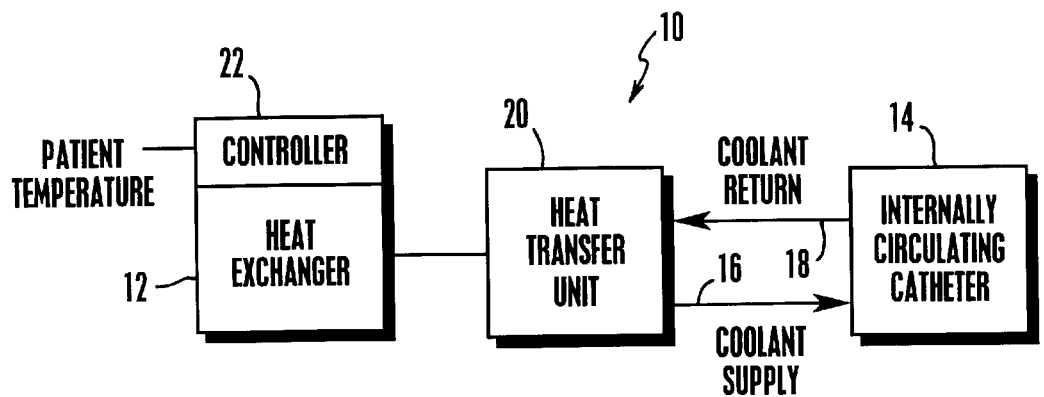
Figure 1  System
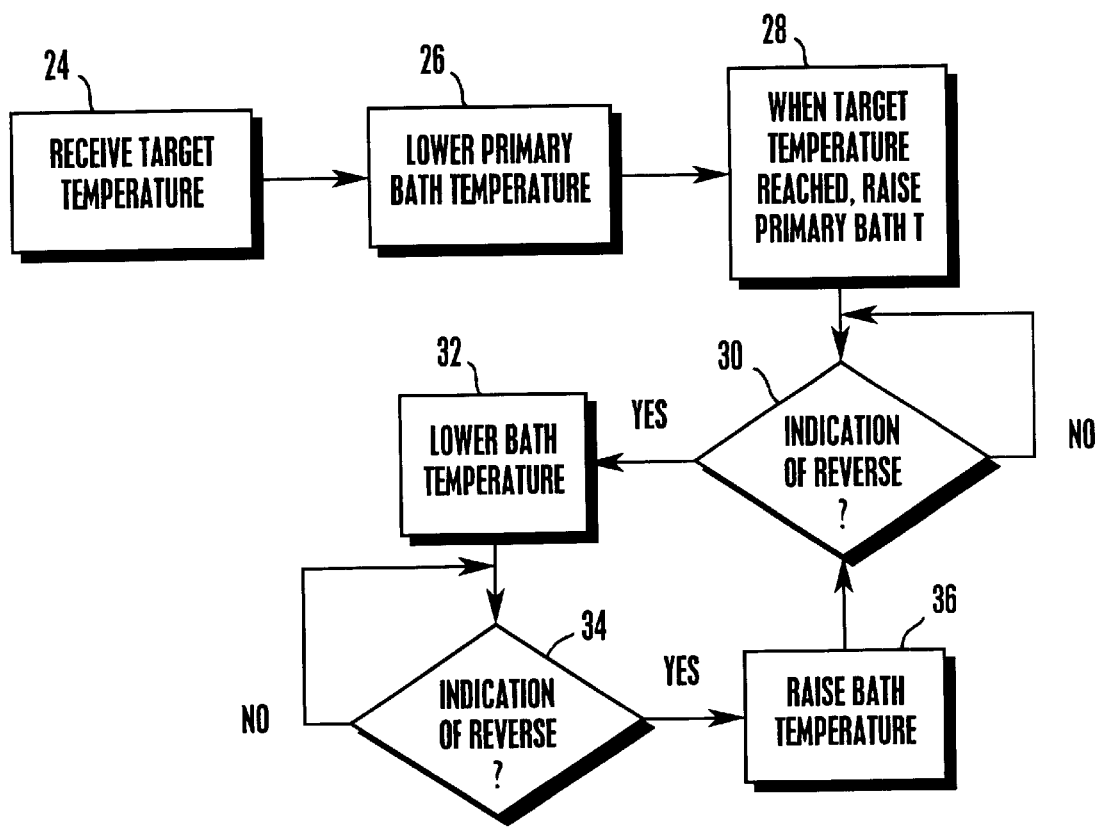
Figure 2  Control Logic

SYSTEM AND METHOD FOR CONTROLLING PATIENT TEMPERATURE

FIELD OF THE INVENTION

The present invention relates generally to patient temperature management using internal heat exchange.

BACKGROUND

The present assignee's U.S. patent application Ser. No. 09/220,897, now U.S. Pat. No. 6,146,411, discloses a cooling system for controlling the temperature of coolant that is circulated through a heat exchange catheter such as that disclosed in the present assignee's co-pending U.S. patent application Ser. No. 09/253,109, now abandoned, both of which are incorporated herein. This application discloses a control method for establishing the temperature of the water bath in the cooling system.

SUMMARY OF THE INVENTION

A controller for a heat exchanger that heats and cools saline flowing through a closed loop heat exchange catheter cools the saline to achieve a target temperature, and then immediately upon reaching target temperature heats the saline. Upon detection of, e.g., a slight patient temperature rise, the controller cools the saline again, with the control loop continuing to tightly control patient temperature in a narrow band around the target temperature.

Accordingly, in one aspect a method for managing patient temperature includes advancing a cooling catheter into a patient. The cooling catheter includes an internally circulating coolant communicating with a heat exchanger. The method includes establishing a target temperature, receiving a patient temperature signal, and causing the heat exchanger to reduce the temperature of the coolant until target temperature is reached. Then, the method includes immediately raising the temperature of the coolant.

In a preferred embodiment, the temperature of the coolant is next lowered in response to receiving an indication that heat exchange should reverse. And again, the temperature of the coolant is raised in response to receiving an indication that heat exchange should reverse.

In another aspect, a system for managing patient temperature to be within a range of a target temperature includes a heat exchange catheter advanceable into a patient, and a heat exchanger. A coolant circulation path is between the catheter and heat exchanger. A controller establishes a temperature in the heat exchanger based at least in part on a sensed patient temperature and a target temperature, with the controller causing the heat exchanger to lower coolant temperature until target temperature is reached and then causing the heat exchanger to immediately raise coolant temperature. In a preferred embodiment, the heat exchanger includes a water bath, and the coolant is in thermal contact with the bath. Also in the preferred embodiment, a heat transfer unit through which coolant flows is disposable in the bath.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a block diagram of the present system; and
FIG. 2 is a flow chart of the present controller.

DETAILED DESCRIPTION OF THE PREFERRED EMBODIMENT

FIG. 1 shows a system 10 that includes a heat exchanger 12 and a cooling catheter 14 that are used to internally cool and heat a patient for establishing and maintaining therapeutic hypothermia or for managing normothermic patient temperature. An example of one type of heat exchanger that can be used to establish the heat exchanger 12 is disclosed in the first of the above-referenced applications, which is incorporated herein by reference, and an example of one type of cooling catheter that can be used to establish the catheter 14 is disclosed in the second of the above-referenced applications, which is incorporated herein by reference. Other catheters that can be used to internally cool or heat a patient include those set forth in Ginsburg U.S. Pat. Nos. 5,486,208, Ginsburg U.S. Pat. No. 5,837,003, Ginsburg U.S. Pat. No. 6,110,168 and Dobak, III et al. U.S. Pat. No. 6,096,068.

In general operation, the system 10 works as follows. Coolant such as saline is circulated through the catheter 14, which can include one or more heat exchange elements such as balloons on its distal end. The heat exchange elements are advanced into a patient, preferably a patient's central venous system through the jugular, subclavian or femoral vein. The coolant circulates through the catheter between a coolant supply line 16 and a coolant return line 18, with the coolant being in thermal contact with the heat exchanger 12 for establishing the temperature of the coolant depending on the desired patient temperature. In a preferred embodiment, the thermal contact is provided by a heat transfer unit 20 which can be advantageously implemented by a tubing pack. Essentially, the tubing pack is a continuation of the supply and return lines 16, 18. In turn, the heat transfer unit 20 can be immersed in a water bath of the heat exchanger 12, such that the temperature of the water bath establishes the temperature of the coolant flowing through the catheter 14. A pump (not shown) engages the tubing to pump the coolant through its circuit.

The heat exchanger 12 has a controller 22 that receives a signal representative of patient temperature. Any patient temperature can be used but in a preferred embodiment bladder, rectal, or esophageal temperature is used. The heat exchanger 12 is preferably a compressor-based system, and the controller 22 controls the compressor as required to establish the temperature of the water bath. The controller 22 can be implemented by software or hardware logic circuits or integrated circuits or analog electronics. In any case, the details of the construction of the preferred heat exchanger 12 are set forth in the first of the above-referenced applications.

Of importance to the present invention is the algorithm implemented by the controller 22. This algorithm can be appreciated in reference to FIG. 2. At block 24, a desired patient target temperature is received by, e.g., a medical caregiver setting a desired temperature in to the heat exchanger 12. For maintaining normothermia, this temperature will usually be on the low end of what is considered normothermia, e.g., around 36.5 or 37 C. At block 26, assuming that the patient is hyperthermic or that it is otherwise desirable to lower the patient's temperature, the temperature of the bath is reduced. This in turn lowers the temperature of the coolant flowing through the catheter 14, which in turn cools the patient.

At block 28, when target temperature is reached as indicated by the patient temperature input to the controller 22, the controller 22 immediately causes the water bath to heat up, adding heat to the coolant. One way to indicate target temperature being reached is to observe a zero difference between target temperature and patient temperature. Equivalently, the reaching of target temperature can be indicated by observing a change in the sign of the difference between target and patient temperatures. At decision diamond 30, it is next determined whether there is any indication that a reversal of the heat exchange should occur. For instance, as soon as patient temperature starts to rise, the test at decision diamond 30 can go positive. Or, as soon as a patient temperature marginally in excess of target temperature is sensed, the test can go positive. In any case, some tolerance can be allowed, e.g., to keep the patient temperature within ±0.2 C. of target temperature.

Once the test at decision diamond 30 goes positive, the logic moves to block 32 where the water bath temperature is once again lowered. Then, at decision diamond 34, the inverse of the decision made at decision diamond 30 is made to determine whether there is any indication that a reversal of the heat exchange should occur. For instance, as soon as patient temperature starts to decrease, the test at decision diamond 34 can go positive. Or, as soon as target temperature is reached, the test can go positive. In any case, some tolerance can be allowed, e.g., to keep the patient temperature within ±0.2 C. of target temperature.

When the test at decision diamond 34 goes positive, the water bath temperature is raised again at block 36 to add heat to the patient. The process continues through the control loop by returning to decision diamond 30.

While the particular SYSTEM AND METHOD FOR CONTROLLING PATIENT TEMPERATURE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A method for managing patient temperature, comprising:

advancing a cooling catheter into a patient, the cooling catheter including an internally circulating coolant communicating with a heat exchanger:

establishing a target temperature;

receiving a patient temperature signal;

causing the heat exchanger to reduce the temperature of the coolant until said target temperature is reached; then immediately raising the temperature of the coolant.

2. The method of claim 1, further comprising lowering the temperature of the coolant after the raising act in response to receiving an indication that heat exchange should reverse.

3. The method of claim 2, further comprising raising the temperature of the coolant after the lowering act in response to receiving an indication that heat exchange should reverse.

4. A system for managing patient temperature to be within a range of a target temperature, comprising:

at least one heat exchange catheter advanceable into a patient;

at least one heat exchanger;

at least one coolant circulation path between the catheter and heat exchanger; and at least one controller establishing a temperature in the heat exchanger based at least in part on a sensed patient temperature and a target temperature, the controller causing the heat exchanger to lower coolant temperature until said target temperature is reached, the controller then causing the heat exchanger to immediately raise coolant temperature.

5. The system of claim 4, wherein the heat exchanger includes a water bath, and the coolant is in thermal contact with the bath.

6. The system of claim 5, further comprising at least one heat transfer unit through which coolant flows, the heat transfer unit being disposable in the bath.

* * * * *